(12) United States Patent
Chun

(10) Patent No.: US 8,702,689 B2
(45) Date of Patent: Apr. 22, 2014

(54) SYSTEMS AND METHODS FOR TWISTING AN EXPANSION ELEMENT OF A CRYOABLATION SYSTEM

(75) Inventor: Byron Chun, Castro Valley, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 872 days.

(21) Appl. No.: 12/870,541

(22) Filed: Aug. 27, 2010

(65) Prior Publication Data

US 2011/0054452 A1 Mar. 3, 2011

Related U.S. Application Data

(60) Provisional application No. 61/238,998, filed on Sep. 1, 2009.

(51) Int. Cl.
*A61B 18/02* (2006.01)
(52) U.S. Cl.
USPC .............................. 606/21; 606/41
(58) Field of Classification Search
USPC ....................................... 606/21, 41
See application file for complete search history.

(56) References Cited

U.S. PATENT DOCUMENTS

| | | | |
|---|---|---|---|
| 4,362,150 A | 12/1982 | Lombardi, Jr. et al. | |
| 4,619,263 A | 10/1986 | Frisbie et al. | |
| 5,090,957 A | 2/1992 | Moutafis et al. | |
| 5,897,567 A | 4/1999 | Ressemann et al. | |
| 6,719,773 B1 | 4/2004 | Boucher et al. | |
| 2006/0282150 A1 | 12/2006 | Olson et al. | |
| 2007/0142818 A1 | 6/2007 | Webler et al. | |
| 2007/0250050 A1* | 10/2007 | Lafontaine ...................... 606/21 |
| 2008/0051818 A1 | 2/2008 | Phan et al. | |

* cited by examiner

*Primary Examiner* — Bill Thomson
*Assistant Examiner* — Jeffrey Lipitz
(74) *Attorney, Agent, or Firm* — Seager, Tufte & Wickhem, LLC

(57) ABSTRACT

A cryoablation catheter assembly includes a catheter that defines at least one coolant outtake region and receives a rotatable guide tube and a coolant transfer tube. The coolant transfer tube receives and transfers coolant from a coolant source to a distal end of the coolant transfer tube. An expansion element is coupled to a distal portion of the catheter and defines an inner expansion-element space. The inner expansion-element space is in fluid communication with the at least one coolant outtake region and the distal end of the coolant transfer tube. A distal end of the expansion element couples to the guide tube. A rotation system is coupleable to, or coupled to, a proximal end of the guide tube and rotates the distal end of the expansion element relative to the proximal end of the expansion element by rotating the guide tube relative to the catheter.

15 Claims, 9 Drawing Sheets

SYSTEMS AND METHODS FOR TWISTING AN EXPANSION ELEMENT OF A CRYOABLATION SYSTEM

RELATED APPLICATIONS

This application claims the benefit of U.S. Provisional Application Ser. No. 61/238,998, filed Sep. 1, 2009, the entire disclosure of which is incorporated herein by reference.

TECHNICAL FIELD

The present invention is directed to the area of cryoablation systems and methods of making and using the systems. The present invention is also directed to cryoablation systems that include a rotation system configured and arranged for twisting an expansion element of a cryoablation system, as well as systems and methods of making and using the rotation systems, expansion elements, and cryoablation systems.

BACKGROUND

Cryoablation systems have been used to reduce, or even eliminate, undesired electrical activity between adjacent cardiac tissues of the heart (arrhythmias). One common type of arrhythmia, atrial fibrillation, is a result of abnormal electrical signals interfering with the normal electrical signal propagation along the tissues of the heart. Atrial fibrillation often originates near the ostia of the pulmonary veins. Cryoablation systems can be used to form lesions on patient tissue in proximity to the ostia, where the pulmonary veins open into the left atrium of the heart. The cold-induced lesions can effectively block the initiation or propagation of the abnormal electrical signals, thereby preventing the abnormal electrical signals from interfering with the normal electrical signal propagation along the tissues of the heart.

BRIEF SUMMARY

In one embodiment, a cryoablation catheter assembly includes a catheter, a rotatable guide tube, a coolant transfer tube, an expansion element, and a rotation system. The catheter has a distal portion, a proximal portion, and a longitudinal length. The catheter is configured and arranged for insertion into patient vasculature. The catheter includes a body and defines at least one coolant outtake region extending along at least a portion of the catheter. The rotatable guide tube is disposed in the catheter. The guide tube has a proximal end and a distal end. The guide tube extends along at least a portion of the catheter such that the distal end of the guide tube extends beyond the distal portion of the catheter. The coolant transfer tube is disposed in the catheter. The coolant transfer tube has a distal end. The coolant transfer tube extends along at least a portion of the catheter such that the distal end of the coolant transfer tube extends beyond the distal portion of the catheter. The coolant transfer tube defines a lumen that is configured and arranged to receive and transfer coolant from a coolant source to the distal end through the coolant transfer tube. The expansion element is coupled to the distal portion of the catheter and has a proximal end, a distal end, and defines an inner expansion-element space. The proximal end couples to the body of the catheter and the distal end couples to the guide tube. The inner expansion-element space is in fluid communication with the at least one coolant outtake region and the distal end of the coolant transfer tube. The rotation system is coupleable to, or coupled to, the proximal end of the guide tube. The rotation system is configured and arranged to rotate the distal end of the expansion element relative to the proximal end of the expansion element by rotating the guide tube relative to the catheter.

In another embodiment, a cryoablation system includes a catheter, a rotatable guide tube, a coolant transfer tube, an expansion element, a rotation system, a coolant source, a fluid-drawing source, and a control module. The catheter has a distal portion, a proximal portion, and a longitudinal length. The catheter is configured and arranged for insertion into patient vasculature. The catheter includes a body and defines at least one coolant outtake region extending along at least a portion of the catheter. The rotatable guide tube is disposed in the catheter. The guide tube has a proximal end and a distal end. The guide tube extends along at least a portion of the catheter such that the distal end of the guide tube extends beyond the distal portion of the catheter. The coolant transfer tube is disposed in the catheter. The coolant transfer tube has a distal end. The coolant transfer tube extends along at least a portion of the catheter such that the distal end of the coolant transfer tube extends beyond the distal portion of the catheter. The coolant transfer tube defines a lumen that is configured and arranged to receive and transfer coolant from a coolant source to the distal end through the coolant transfer tube. The expansion element is coupled to the distal portion of the catheter and has a proximal end, a distal end, and defines an inner expansion-element space. The proximal end couples to the body of the catheter and the distal end couples to the guide tube. The inner expansion-element space is in fluid communication with the at least one coolant outtake region and the distal end of the coolant transfer tube. The rotation system is coupleable to, or coupled to, the proximal end of the guide tube. The rotation system is configured and arranged to rotate the distal end of the expansion element relative to the proximal end of the expansion element by rotating the guide tube relative to the catheter. The coolant source couples to the coolant transfer tube. The fluid-drawing source couples to the at least one coolant outtake region. The control module couples to the catheter, the coolant source, and the fluid-drawing source. The control module includes a coolant flow controller that is configured and arranged for controlling the flow of coolant along the coolant transfer tube and the at least one coolant outtake region.

In yet another embodiment, a method for cryoablating patient tissue includes inserting a catheter in patient vasculature. The catheter has a distal portion, a proximal portion, and a longitudinal length. The catheter includes a body and defines at least one coolant outtake region. The catheter receives a guide tube and a coolant transfer tube that each extend along at least a portion of the catheter. The guide tube extends beyond the distal portion of the catheter. The catheter is guided in proximity to patient tissue to be ablated. Coolant is drawn from a coolant source such that coolant flows along the coolant transfer tube and is sprayed into an expansion element that is disposed at the distal portion of the catheter, thereby expanding the expansion element and reducing the temperature of the expansion element to a temperature sufficiently low enough to ablate patient tissue upon contact. A distal end of the expansion element is coupled to the guide tube and a proximal end of the expansion element is coupled to the body of the catheter. Patient tissue is contacted with the expanded expansion element for a time period adequate to ablate tissue contacting the expansion element. The expansion element is deflated by drawing the coolant along the at least one coolant outtake region from the expansion element. A proximal end of the guide tube is rotated in relation to the catheter using a coupled rotation system. The rotation system includes a linear gear assembly coupled to a rotational gear assembly. The rotation of the guide tube causes the distal end of the expansion element to rotate, thereby causing the expansion element to twist.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified. For a better understanding of the present invention, reference will be made to the following Detailed Description, which is to be read in association with the accompanying drawings, wherein.

DETAILED DESCRIPTION

The present invention is directed to the area of cryoablation systems and methods of making and using the systems. The present invention is also directed to cryoablation systems that include a rotation system configured and arranged for twisting an expansion element of a cryoablation system, as well as systems and methods of making and using the rotation systems, expansion elements, expansion elements, and cryoablation systems.

A cryoablation system can include a catheter configured and arranged for transporting coolant to and from a target location within a patient, an expansion element disposed at a distal portion of the catheter for ablating contacted patient tissue, a coolant source coupled to the catheter for supplying the coolant, and a control module for controlling or monitoring one or more of the operations of the system (e.g., controlling coolant flow, monitoring catheter pressure or temperature, or the like). The expansion element can be positioned at a target location in patient vasculature (e.g., the left atrium of the heart) and the coolant can be input to the catheter and directed to the expansion element. When the coolant contacts the expansion element, the coolant absorbs heat and expands, thereby causing the expansion element to expand and reduce in temperature to a level low enough to ablate patient tissue upon contact. The coolant flows out of the expansion element and back to a proximal end of the catheter. As the coolant flows out of the expansion element, the expansion element deflates and the catheter may be removed from the patient vasculature.

Figure 1:
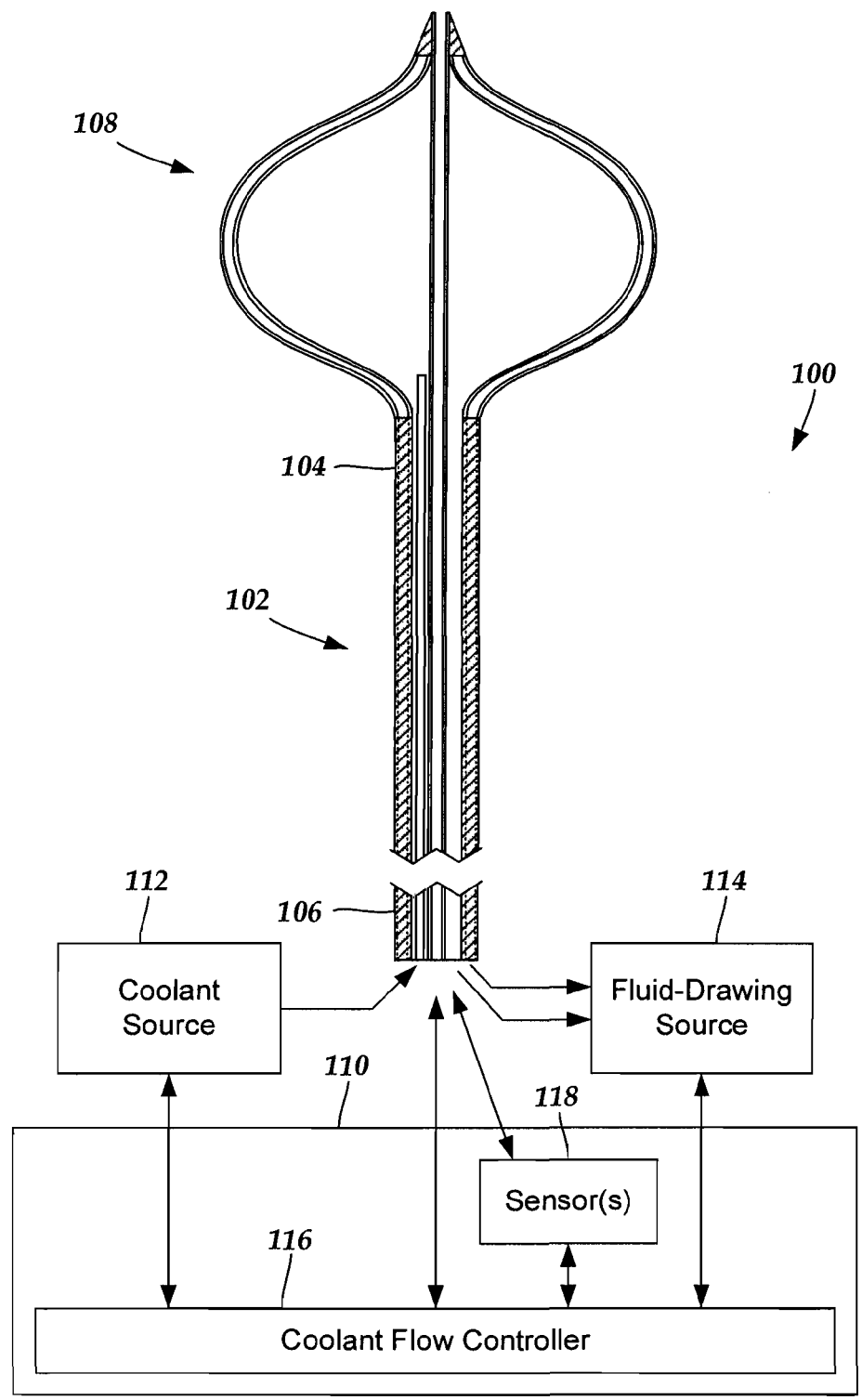
FIG. 1 is a schematic partial cross-sectional and partial block diagram view of one embodiment of a cryoablation system, according to the invention.

FIG. 1 illustrates schematically one embodiment of a cryoablation system 100. The cryoablation system 100 includes a catheter 102 with a distal portion 104 and a proximal portion 106. An expansion element 108 is coupled to the distal portion 104 of the catheter 102. A control module 110, a coolant source 112, and a fluid-drawing source 114 (e.g., a vacuum source, a pump, or the like) are each coupled to the proximal portion 106 of the catheter 102. The control module 110 includes a coolant flow controller 116 to control the flow of coolant within the catheter 102 to and from the expansion element 108. In at least some embodiments, the control module 104 also includes one or more sensors 118 for monitoring one or more conditions (e.g., pressure, temperature, or the like) within the catheter 102.

In at least some embodiments, the coolant source 112 includes a coolant under pressure. A variety of different coolants may be used to provide a low enough temperature to ablate tissue upon contact. In preferred embodiments, the coolant is a low freezing point liquid with a low vaporization temperature which may be input to the catheter 102 as a liquid that is sprayed into the expansion element 108, where the liquid coolant absorbs heat and is vaporized or atomized. Examples of suitable liquids include, but are not limited to, a liquefied gas (e.g., nitrogen, nitrous oxide, carbon dioxide, or the like), one or more chlorofluorocarbons, one or more hydrochlorofluorocarbons, ethanol mixtures, saline solutions, or the like. It will be understood that a combination of one or more coolants may be used in the cryoablation system 100.

Figure 2A:
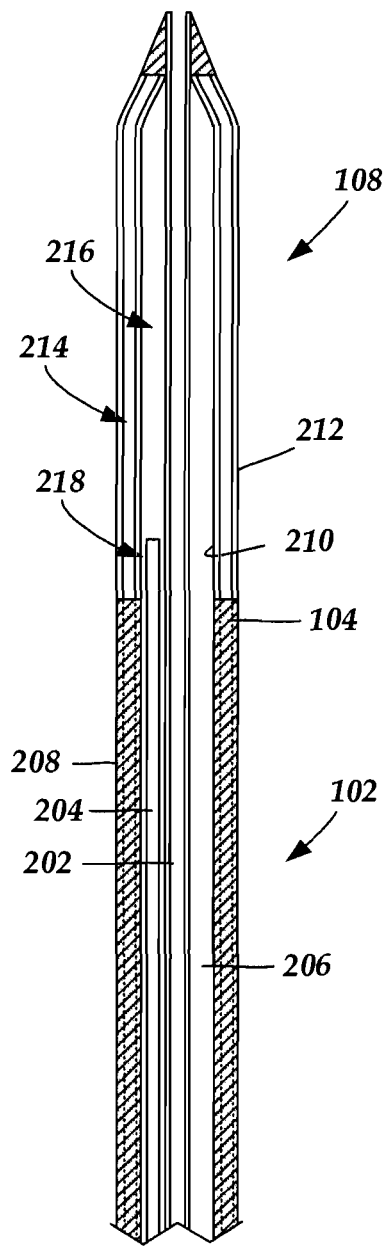
FIG. 2A is a schematic longitudinal cross-sectional view of one embodiment of an expansion element coupled to a distal portion of a catheter of the cryoablation system of FIG. 1, the expansion element in a deflated configuration, according to the invention.

During a typical cryoablation procedure, the distal portion 104 of the catheter 102 is inserted into patient vasculature for delivery of the expansion element 108 to an ablation site. FIG. 2 A is a schematic longitudinal cross-sectional view of one embodiment of the distal portion 104 of the catheter 102 and the expansion element 108. In FIG. 2 A, the expansion element 210 is shown in a deflated configuration. A guide tube 202, a coolant transfer lumen 204, and at least one coolant outtake region 206 are each disposed in a flexible body 208 of the catheter 102. In at least some embodiments, the material(s) used to form the body 208 is braided. In at least some embodiments, a braided support may be used to add support to the body 208.

In some embodiments, the expansion element 108 includes a single layer. In other embodiments, the expansion element 108 includes multiple layers. For example, in at least some embodiments, the expansion element 108 includes an inner layer 210 and an outer layer 212 disposed over the inner layer 210. FIGS. 1-3, 5, and 6 show the expansion element 108 having two layers. It will be understood that the expansion element 108 may, instead, only have a single layer, or may have more than two layers.

In at least some embodiments, a vacuum is maintained between the inner layer 210 and the outer layer 212 (i.e., in an intra expansion-element space 214). In at least some embodiments, the intra expansion-element space 214 is in fluid communication with the fluid-drawing source 114. In at least some embodiments, a proximal end of the expansion element 108 couples to the distal portion 104 of the catheter 104, such as the flexible body 208, such that a region within the expansion element 108 (i.e., an inner expansion-element space 216) is in fluid communication with the at least one coolant outtake region 206.

The expansion element 108 may be formed from any elastic or semi-elastic material, such as one or more thermoplastics (e.g., polyether block amide, or the like), or other plastics (e.g., nylon, urethane, or the like) that maintain elasticity over a wide range of temperatures, particularly at the temperature of the expanded coolant. In at least some embodiments, the expansion element 108 is semi-elastic, wherein the size of the expansion element 108 does not change in response to incremental changes in pressure that are below 5 psi (about 34.5× 10 Pa).

The guide tube 202 may be formed from any flexible material (e.g., a thermoplastic, or the like) that maintains elasticity over a wide range of temperatures, particularly at the temperature of the expanded coolant. In at least some embodiments, the material(s) used to form the guide tube 202 is braided. In at least some embodiments, a braided support may be used to add support to the guide tube 202. The guide tube 202 is optionally configured and arranged to receive a stiffening member (e.g., a stylet, or the like) to facilitate guiding of the catheter 102 to a target location within patient vasculature by providing additional rigidity to the catheter 102. In at least some embodiments, the guide tube 202 defines a lumen through which the stiffening member can be extended. In at least some embodiments, the guide tube extends along a longitudinal length of the catheter 102 from the proximal portion (106 in FIG. 1) of the catheter 102 to a position that is beyond the distal portion 104 of the catheter 102. In at least some embodiments, the distal end of the expansion element 108 is coupled to the guide tube 202.

The coolant transfer tube 204 extends along the longitudinal length of the catheter 102 from the proximal portion (106 in FIG. 1) of the catheter 102. The coolant transfer tube 204 defines a lumen. A proximal end of the lumen is coupled to the coolant source (112 in FIG. 1). The coolant transfer tube 204 includes a distal end 218 that opens into the inner expansion-element space 216. In at least some embodiments, the distal end 218 of the coolant transfer tube 204 extends beyond the distal portion of the catheter 102 and into the inner expansion-element space 216.

The coolant outtake region 206 is configured and arranged to accommodate coolant exiting the expansion element 108. The coolant outtake region 206 extends along the longitudinal length of the catheter 102 from the proximal portion (106 in FIG. 1) of the catheter 102 to the expansion element 108. In some embodiments, the coolant outtake region 206 includes one or more tubes that define one or more lumens. In other embodiments, the coolant outtake region 206 includes one or more open regions within the body 208 of the catheter 102 and exterior to the guide tube 202 and the coolant transfer tube 204. In at least some embodiments, a proximal end of the coolant outtake region 206 is in fluid communication with the fluid-drawing source (114 in FIG. 1).

The distal end 218 of the coolant transfer tube 204 is configured and arranged to output coolant from the coolant transfer tube 204 to the inner expansion-element space 216. In at least some embodiments, the distal end 218 of the coolant transfer tube 204 is open. In at least some embodiments, the distal end 218 of the coolant transfer tube 204 defines one or more spray apertures. In at least some embodiments, the coolant is output as a sprayed liquid that vaporizes or atomizes as the liquid is output from the distal end 218 of the coolant transfer tube 204. In at least some embodiments, when the coolant enters the inner expansion-element space 216, the expansion element 108 absorbs heat and expands, thereby reducing the temperature of the expansion element 108 to a temperature sufficiently low enough to ablate patient tissue upon contact.

The reduction in temperature of the expansion element 108 may be due to one or more of the Joule-Thompson effect or the latent heat of vaporization. The Joule-Thompson effect describes the cooling effect that comes about when a compressed non-ideal gas expands into a region of low pressure (e.g., within the expansion element 108). The latent heat of vaporization describes heat being released as a result of the phase change from a liquid to a gas (e.g., the liquefied coolant vaporizing upon entering the expansion element 108).

Figure 2B:
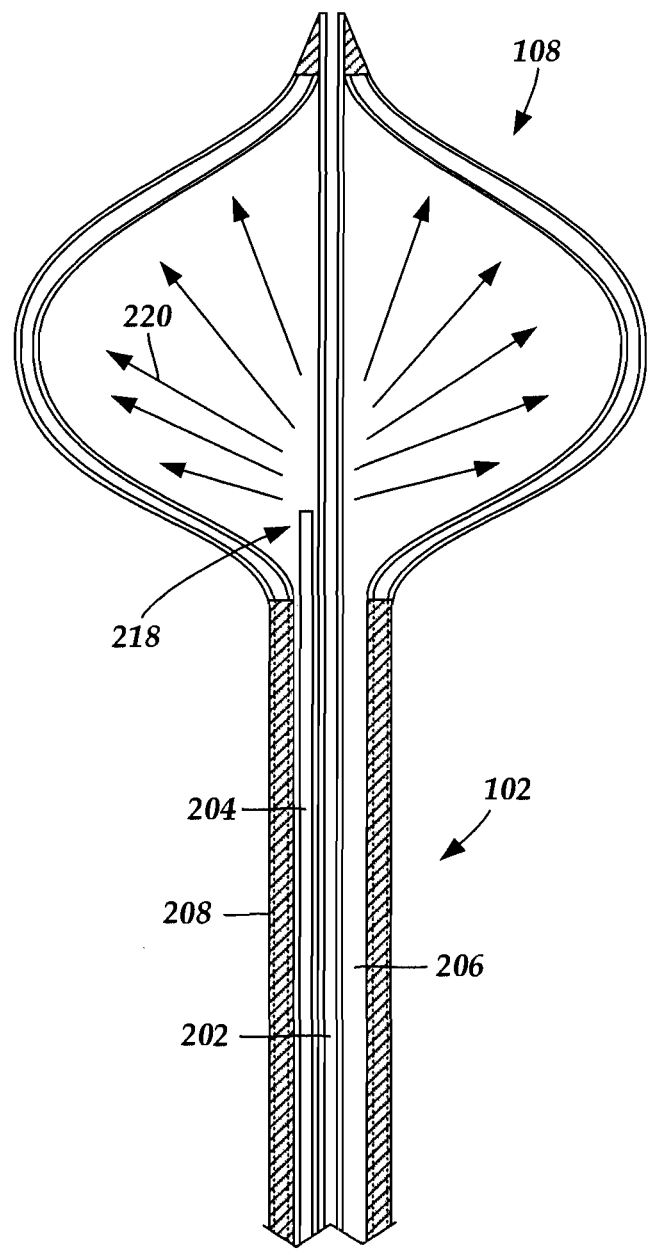
FIG. 2B is a schematic longitudinal cross-sectional view of one embodiment of an expansion element coupled to a distal portion of a catheter of the cryoablation system of FIG. 1, the expansion element in an inflated configuration, according to the invention.

FIG. 2B is a schematic longitudinal cross-sectional view of one embodiment of the expansion element 108 in an inflated configuration. Directional arrows, such as arrow 220, show the flow of coolant from the distal end 218 of the coolant transfer tube 204 to the inner expansion-element space 216. The expanded gas dissipates down the catheter 102 along the coolant outtake region 206. In at least some embodiments, the fluid-drawing source (114 in FIG. 1) is used to draw the expanded, heated, and gaseous coolant along the coolant outtake region 206 from the expansion element 108 out the proximal end of the coolant outtake region 206.

Typically, the catheter 102 is inserted in patient vasculature and guided to an ablation site, such as the ostia of the pulmonary veins in the left atrium of the heart of the patient. In at least some embodiments, the expansion element 108 is maintained in a vacuum during insertion. Once the expansion element is in proximity to the ablation site, coolant from the coolant source (106 in FIG. 1) may be released into the catheter 102. In at least some embodiments, the coolant source 106 includes a pressurized container or pump. In at least some embodiments, the lower pressure in the expansion element 108 draws the coolant along the coolant transfer tube 104 and into the expansion element 108. In at least some embodiments, the fluid-drawing source (114 in FIG. 1) may be used to control the rate of flow of the coolant within the catheter 102. The rate of flow of the coolant within the catheter 102 may be adjusted to a rate appropriate to the specific type of operation.

In some embodiments, a cryoablation procedure involves ablating patient tissue at multiple ablation sites. When multiple tissue ablations are performed, the expansion element 108 may be deflated between one or more of the tissue ablations and moved to the next ablation site. In at least some embodiments, the expansion element 108 is deflated between one or more of the tissue ablations to an ambient pressure. Deflation of the expansion element 108 after a tissue ablation may result in the expansion element 108 forming an unpredictable shape. Some shapes may make movement of the catheter 102 (or retraction of the expansion element 108 after completion of each ablation) difficult to achieve. Thus, it would be advantageous for the expansion element to deflate to a predictable shape that facilitates subsequent movement or retraction of the expansion element 108.

A rotation system can be used to twist the expansion element. In at least some embodiments, the rotation system can be used to twist the expansion element during deflation of the expansion element, thereby causing the expansion element to deflate into a predictable shape with a profile that may facilitate movement or retraction of the expansion element. In at least some embodiments, the rotation system twists the expansion element by rotating the guide tube. As discussed above and as shown in FIG. 2B, the expansion element 108 is coupled at a distal end to the guide tube 202 and at a proximal end to the body 208 of the catheter 102. Thus, in at least some embodiments, rotation of the guide tube 202 relative the catheter 102 causes the expansion element 108 to twist.

Figure 3:
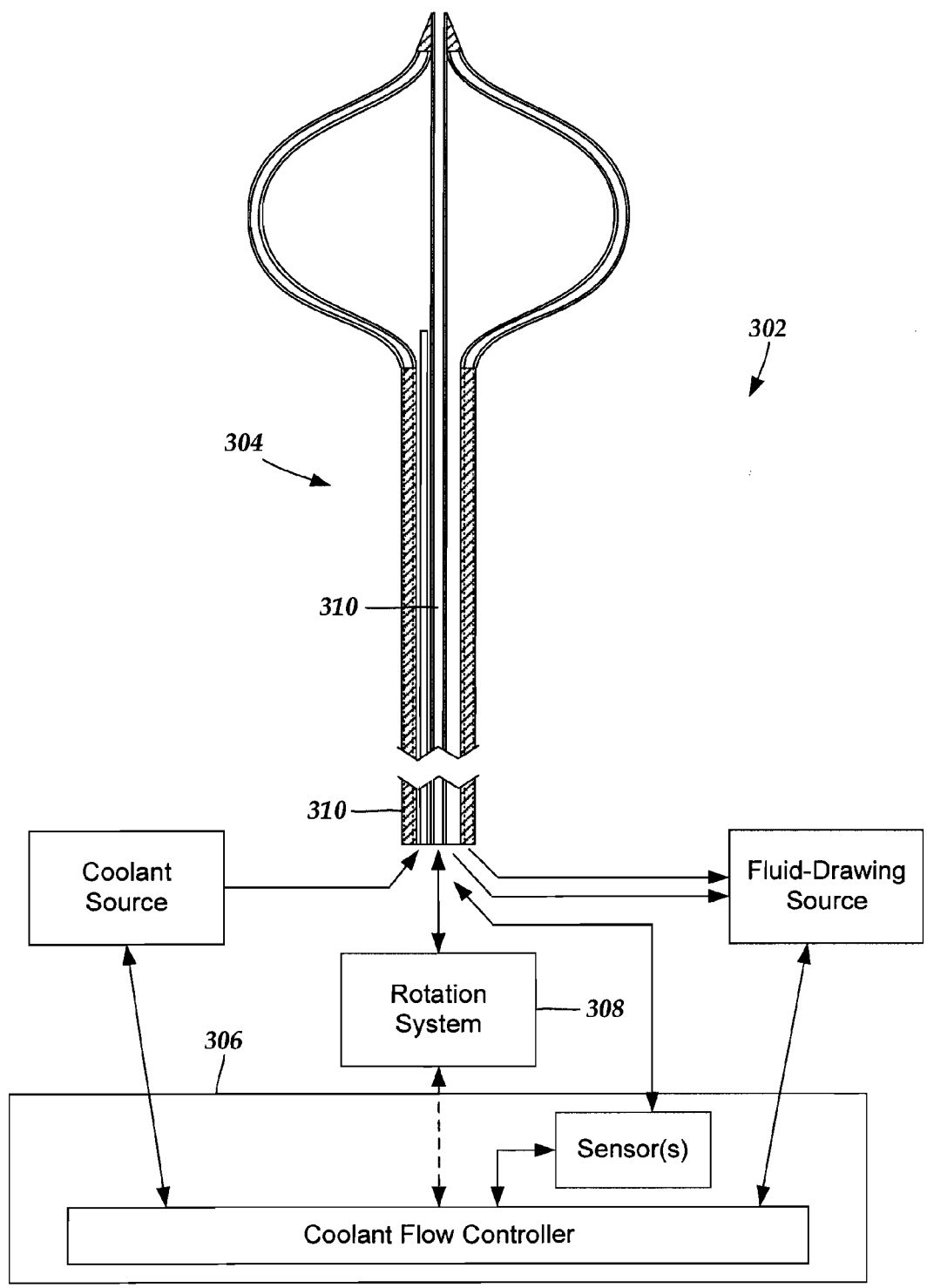
FIG. 3 is a schematic partial cross-sectional and partial block diagram view of another embodiment of a cryoablation system, the cryoablation system including a rotation system, according to the invention.

FIG. 3 is a schematic partial cross-sectional and partial block diagram view of another embodiment of a cryoablation system 302. The cryoablation system 302 includes a catheter 304, a control module 306, and a rotation system 308 that is coupleable to a proximal end 310 of the catheter 302. In at least some embodiments, the rotation system 308 is a standalone device coupled directly to the proximal end 310 of the catheter 302. In at least some embodiments, the rotation system 308 is incorporated into a handle coupleable to the catheter 302. In at least some embodiments, the rotation system 308 is integrated into the control module 306.

Figure 4A:
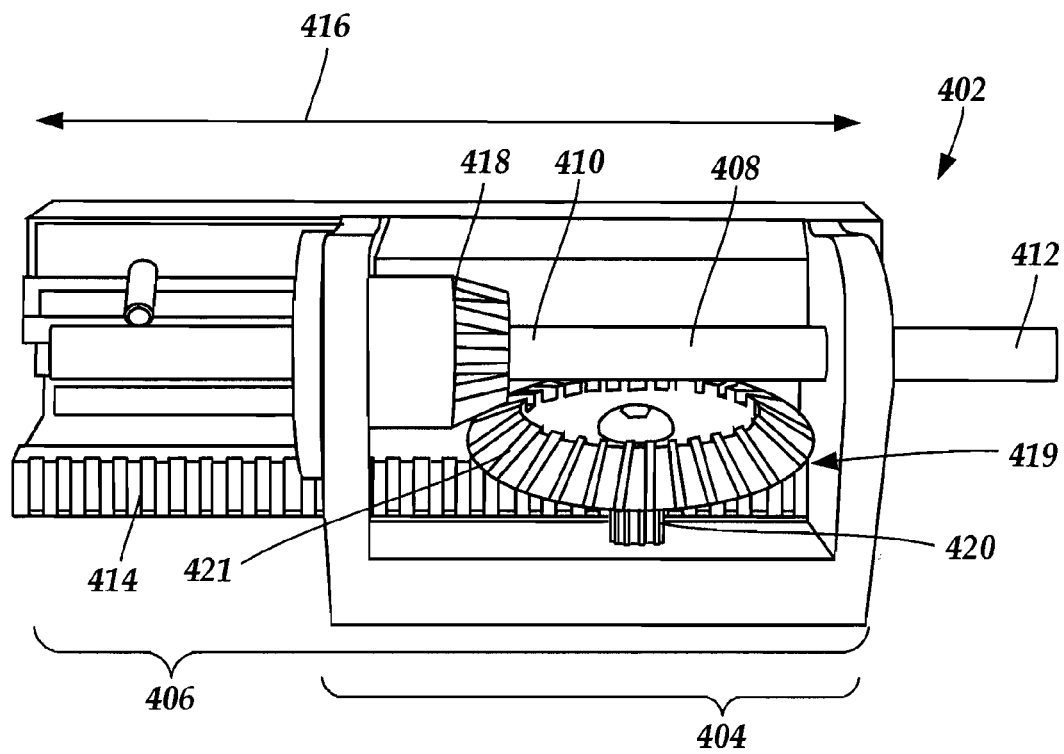
FIG. 4A is a first schematic perspective view of one embodiment of a rotation system configured and arranged for twisting the expansion element of FIG. 2A, according to the invention.

FIG. 4A is a first schematic perspective view of one embodiment of a rotation system 402 configured and arranged for twisting the expansion element (108 in FIG. 1). The rotation system 402 includes a rotational gear assembly 404 mated with a linear gear assembly 406. The rotational gear assembly 404 also includes a shaft 408 with a proximal end 410 coupled to the rotational gear assembly 404 and a distal end 412 coupleable to the guide tube (202 in FIG. 2A).

In at least some embodiments, the rotation system 402 is configured and arranged to convert applied linear motion of the linear gear assembly 406 into rotational motion of the rotational gear assembly 404. The rotational motion of the rotational gear assembly 404 causes the shaft 408 to rotate which, in turn, causes the guide tube (202 in FIG. 2A) to rotate. Rotation of the guide tube 202 relative to the catheter 102 causes the expansion element (108 in FIG. 1) to twist. In at least some embodiments, the shaft 408 is omitted and the guide tube 202 couples directly to the rotational gear assembly 404.

The linear gear assembly 406 includes a flat rack gear 414 with a longitudinal length 416. The rotational gear assembly 404 includes a first beveled gear 418 and a combination gear 419. The combination gear 419 includes a spur gear 420 fixedly coupled to a second beveled gear 421. The proximal end 410 of the shaft 406 is fixedly coupled to the first beveled gear 418 such that rotation of the first beveled gear 418 causes rotation of the shaft 408. In at least some embodiments, the shaft 408 extends in a direction roughly parallel to the axis of the longitudinal length 416 of the rack gear 414.

In at least some embodiments, each of the gears 414 and 418-421 include teeth that mate with teeth of other of the gears 414 and 418-421 to move mating gears 414 and 418-421 relative to one another. The gears 414 and 418-421 can be formed from any durable material including, for example, polyoxymethylene, polyamide (such as nylon, or the like), acetal, metals, or the like or combinations thereof.

In at least some embodiments, applied linear motion of the linear gear assembly 406 causes teeth on the spur gear 420 to interact with teeth on the rack gear 414, thereby causing the spur gear 420 to rotate. The rotation of the spur gear 420 causes rotation of the coupled second beveled gear 421. The rotation of the second beveled gear 421 causes teeth on the second beveled gear 421 to interact with teeth on the first beveled gear 418, thereby causing the first beveled gear 418 to rotate. In at least some embodiments, the teeth of the first beveled gear 418 and the second beveled gear 424 are disposed on beveled faces that couple together such that the first beveled gear 418 and the second beveled gear 424 are oriented in different planes from one another. Thus, the rack-gear/spur-gear interface converts linear motion to rotational motion and the remaining gear interfaces adjust the positioning and the axis of the rotational motion of the shaft 408. In at least some embodiments, the shaft 408 rotates around an axis that is roughly parallel to the axis of the longitudinal length 416 of the rack gear 414. Accordingly, in at least some embodiments, the rotation system 402 is configured and arranged such that linear movement of the linear gear assembly 406 along an axis causes rotational movement of the shaft 408 along the same axis.

Figure 4B:
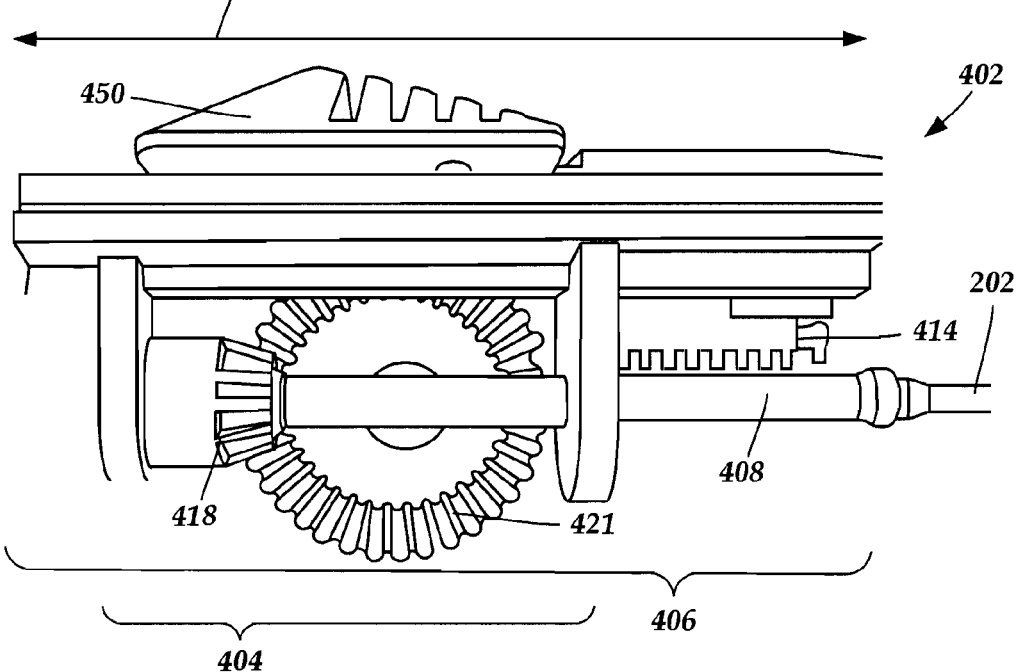
FIG. 4B is a second schematic perspective view of one embodiment of a rotation system configured and arranged for twisting the expansion element of FIG. 2A, according to the invention.

FIG. 4B is a second schematic perspective view of one embodiment of the rotation system 402. In at least some embodiments, application of linear motion of the linear gear assembly 406 is facilitated by a tactile control 450 (e.g., a thumb drive, knob, lever, button, or the like) configured and arranged for use by a user of the cryoablation system (100 in FIG. 1). In at least some embodiments, the tactile control 450 is coupled to the linear gear assembly 406. In at least some embodiments, the tactile control 450 is fixedly coupled to the linear gear assembly 406 such that linear movement of the tactile control 450 causes linear movement of the linear gear assembly 406 along the same axis.

The shaft 408 couples to the guide tube 202. In at least some embodiments, the distal end 412 of the shaft 408 fixedly couples to the proximal end of the guide tube 202. The shaft 408 may couple to the guide tube 202 in many different ways (e.g., a mechanical retention mechanism, adhesive, string, wire, or the like). In at least some embodiments, the shaft 408 is coupled to the guide tube 202 via one or more adapters (not shown). In at least some embodiments, the guide tube 202 couples directly to the rotational gear assembly 404.

In at least some embodiments, gear ratios between mating gears 414 and 418-421 (e.g., between the rack gear 414 and the spur gear 420, and between the first beveled gear 418 and the second beveled gear 421) can be adjusted to alter the amount of force needed to actuate the rotation of the shaft 408 and the number of revolutions the shaft 408 completes during movement of the rotational gear assembly 404 along the longitudinal length 416 of the linear gear assembly 406. In at least some embodiments, the gear ratios are set such that movement of the rotational gear assembly 404 along the longitudinal length 416 of the linear gear assembly 406 causes the guide tube (202 in FIG. 2A) to rotate a specific number of revolutions. In at least some embodiments, the gear ratios are set such that movement of the rotational gear assembly 404 along the longitudinal length 416 of the linear gear assembly 406 causes the expansion element (108 in FIG. 1) to twist a specific number of revolutions.

In at least some embodiments, the number of revolutions completed by the shaft 408 (and the proximal end of the guide tube 202) is not equal to the number of twists completed by the expansion element 108. For example, in at least some embodiments, 2.5 revolutions of the shaft 408 causes the same number of revolutions of a proximal end of the guide tube 202, yet only one revolution of the expansion element (108 in FIG. 1). It will be understood that the differences in the amount of relative rotation of the guide tube 202 to the expansion element 108 may vary depending on a number of factors, such as the length of the guide tube 202, the rigidity of the material from which the guide tube 202 is formed, whether or not the guide tube 202 includes a support sleeve (e.g., a braided support, or the like), the coupling of the shaft 408 to the guide tube 202, the coupling of the guide tube 202 to the expansion element 108, or the like.

In at least some embodiments, the gear ratios are set such that movement of the rotational gear assembly 404 along the longitudinal length 416 of the linear gear assembly 406 causes the guide tube (202 in FIG. 2A) to complete at least one revolution. In at least some embodiments, the gear ratios are set such that movement of the rotational gear assembly 404 along the longitudinal length 416 of the linear gear assembly 406 causes the guide tube (202 in FIG. 2A) to complete at least two revolutions. In at least some embodiments, the gear ratios are set such that movement of the rotational gear assembly 404 along the longitudinal length 416 of the linear gear assembly 406 causes the guide tube (202 in FIG. 2A) to complete at least three revolutions. In at least some embodiments, the gear ratios are set such that movement of the rotational gear assembly 404 along the longitudinal length 416 of the linear gear assembly 406 causes the guide tube (202 in FIG. 2A) to complete at least four revolutions. In at least some embodiments, the gear ratios are set such that movement of the rotational gear assembly 404 along the longitudinal length 416 of the linear gear assembly 406 causes the guide tube (202 in FIG. 2A) to complete at least five revolutions.

In at least some embodiments, the gear ratios are set such that movement of the rotational gear assembly 404 along the longitudinal length 416 of the linear gear assembly 406 causes the expansion element (108 in FIG. 1) to twist at least a half revolution. In at least some embodiments, the gear ratios are set such that movement of the rotational gear assembly 404 along the longitudinal length 416 of the linear gear assembly 406 causes the guide tube (202 in FIG. 2A) to twist at least one revolution. In at least some embodiments, the gear ratios are set such that movement of the rotational gear assembly 404 along the longitudinal length 416 of the linear gear assembly 406 causes the guide tube (202 in FIG. 2A) to twist at least one-and-a-half revolutions. In at least some embodiments, the gear ratios are set such that movement of the rotational gear assembly 404 along the longitudinal length 416 of the linear gear assembly 406 causes the guide tube (202 in FIG. 2A) to twist at least two revolutions.

Figure 5A:
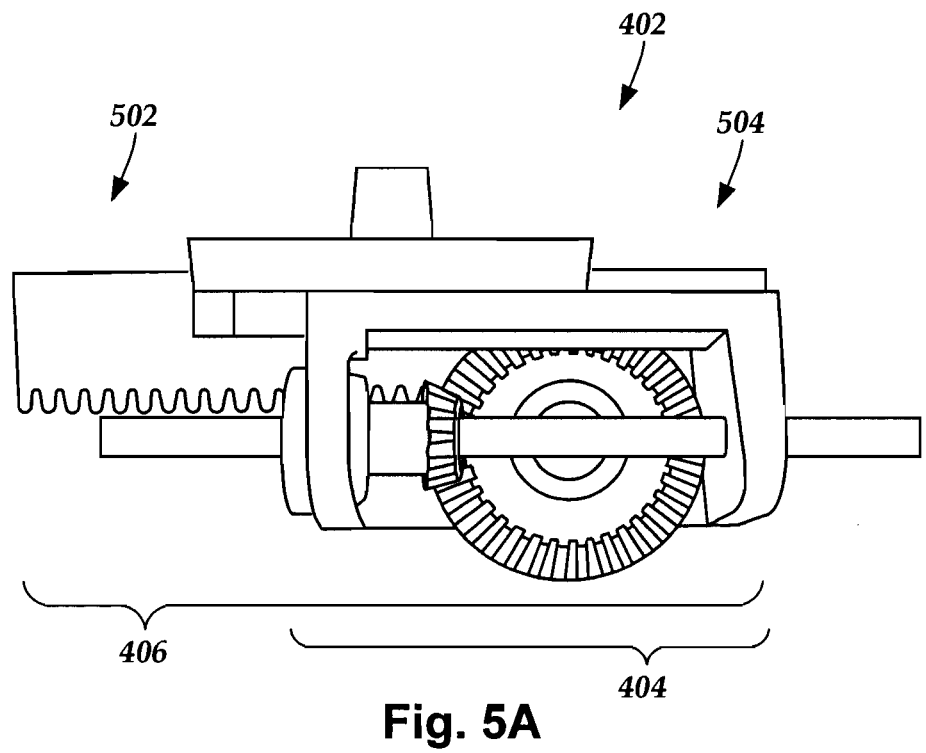
FIG. 5A is a first schematic top view of another embodiment of a rotation system configured and arranged for twisting the expansion element of FIG. 2A, according to the invention.
Figure 5B:
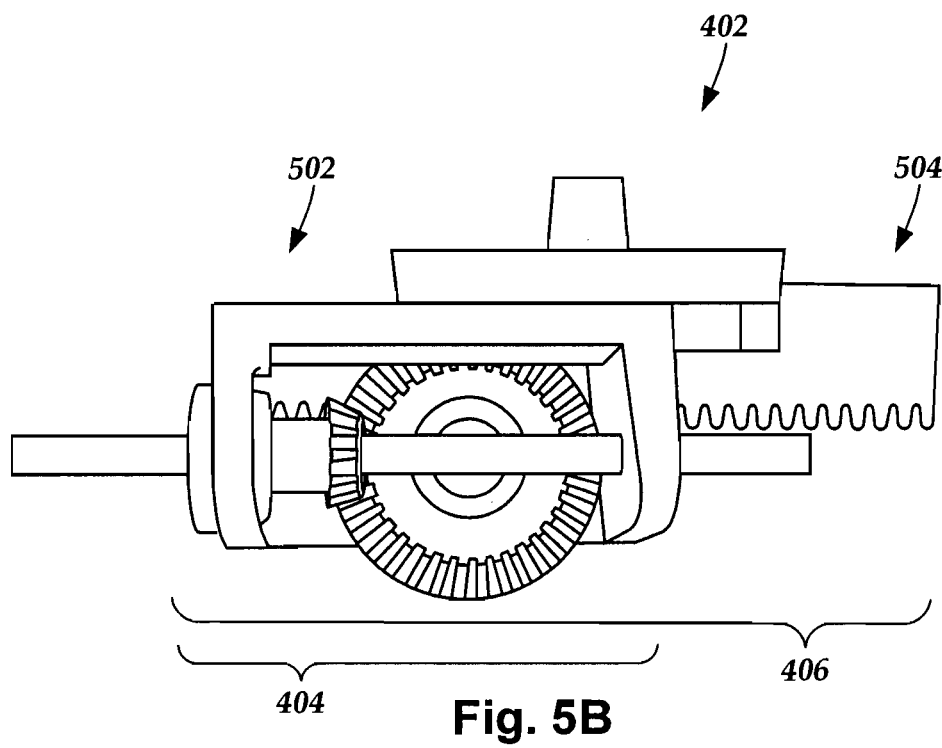
FIG. 5B is a second schematic top view of the embodiment of the rotation system of FIG. 5A, according to the invention.
Figure 5C:
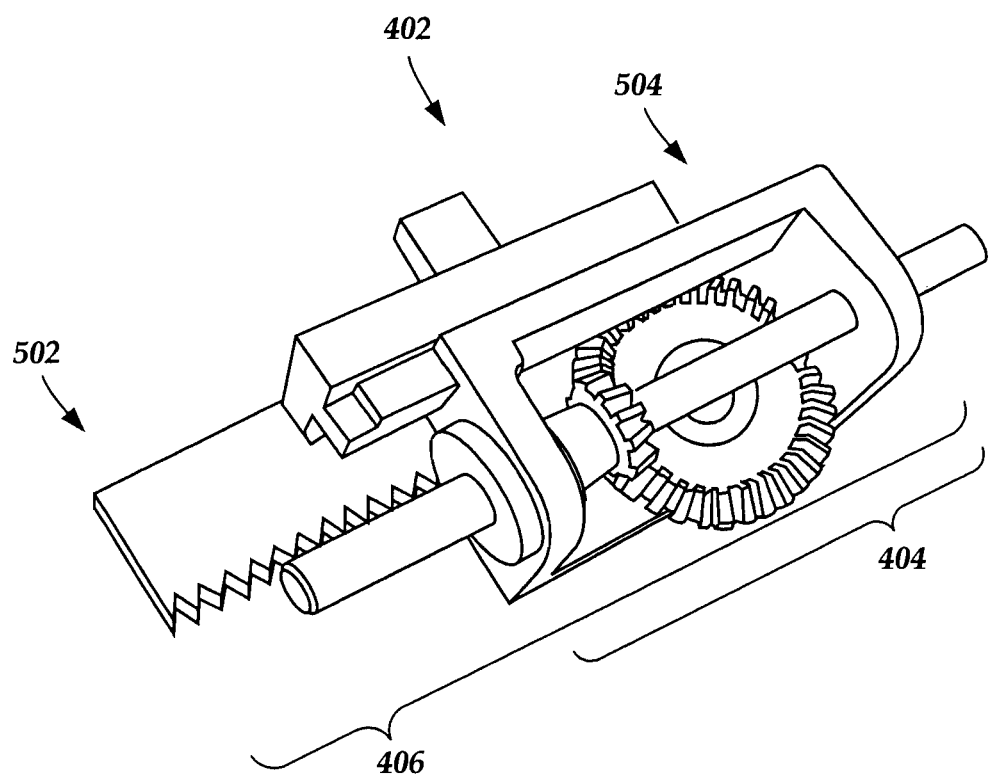
FIG. 5C is a schematic perspective view of the embodiment of the rotation system of FIG. 5A, according to the invention.

FIGS. 5A-5C show another embodiment of the rotation system 402. FIGS. 5A and 5B are schematic top views of the rotation system 402. The linear gear assembly 406 includes a proximal end 502 and a distal end 504. In FIG. 5A, the rotational gear assembly 404 is mated with the linear gear assembly 406 such that the rotational gear assembly 404 is positioned against the distal end 504 of the linear gear assembly 406. In FIG. 5B, the rotational gear assembly 404 has been moved along the linear gear assembly 406 such that the rotational gear assembly 404 is positioned against the proximal end 502 of the linear gear assembly 406. FIG. 5C is a schematic perspective view of the rotational gear assembly 404 of the rotation system 402 positioned against the proximal end 502 of the linear gear assembly 406.

Figure 6:
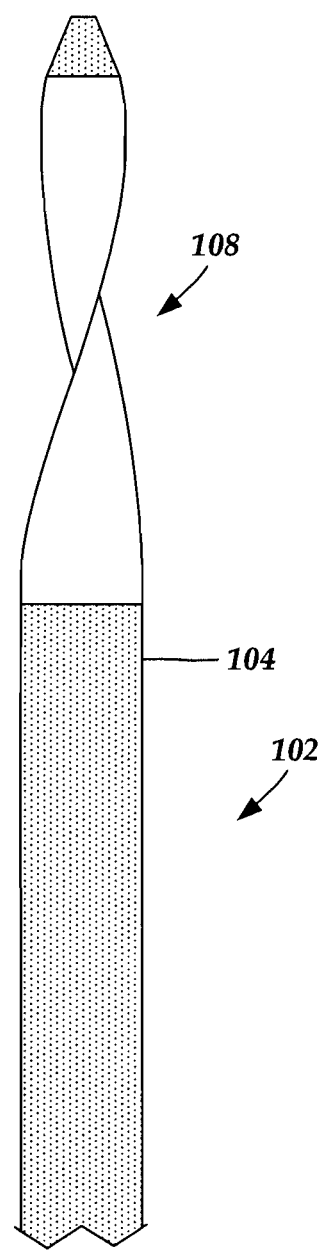
FIG. 6 is a schematic side view of one embodiment of a distal portion of the catheter of FIG. 2A, an expansion element disposed at a distal portion of the catheter twisted by a rotation system, according to the invention.

FIG. 6 is a schematic side view of one embodiment of the distal portion 104 of the catheter 102. In FIG. 6, the expansion element 108 of the catheter 102 is shown twisted a half revolution by the rotation system (308 in FIG. 3). The twisting of the expansion element 108 causes the expansion element 108 to form a predictable shape. In at least some embodiments, the rotation system 308 is used during or after deflation of the expansion element 108. In at least some embodiments, when the expansion element 108 is in proximity to ambient pressure, the profile of the expansion element 108 after twisting is reduced from the profile of the expansion element 108 before twisting.

In at least some embodiments, during an ablation procedure the expansion element 108 is inflated to a pressure that is no more than 2 atm (about $2\times10^5$ Pa). In at least some embodiments, during an ablation procedure the expansion element 108 is inflated to a pressure that is no more than 3 atm (about $3\times10^5$ Pa). In at least some embodiments, during an ablation procedure the expansion element 108 is inflated to a pressure that is no more than 4 atm (about $4\times10^5$ Pa). In at least some embodiments, during an ablation procedure the expansion element 108 is inflated to a pressure that is no more than 5 atm (about $5\times10^5$ Pa). In at least some embodiments, during an ablation procedure the expansion element 108 is inflated to a pressure that is no more than 6 atm (about $6\times10^5$ Pa). In at least some embodiments, during an ablation procedure the expansion element 108 is inflated to a pressure that is no more than 7 atm (about $7\times10^5$ Pa). In at least some embodiments, during an ablation procedure the expansion element 108 is inflated to a pressure that is no more than 8 atm (about $8\times10^5$ Pa). In at least some embodiments, during an ablation procedure the expansion element 108 is inflated to a pressure that is no more than 9 atm (about $9\times10^5$ Pa).

In at least some embodiments, during an ablation procedure the temperature of the expansion element 108 is reduced to a temperature that is no greater than $-20°$ C. In at least some embodiments, during an ablation procedure the temperature of the expansion element 108 is reduced to a temperature that is no greater than $-40°$ C. In at least some embodiments, during an ablation procedure the temperature of the expansion element 108 is reduced to a temperature that is no greater than $-60°$ C. In at least some embodiments, during an ablation procedure the temperature of the expansion element 108 is reduced to a temperature that is no greater than $-80°$ C.

In at least some embodiments, during an ablation procedure the temperature within the expansion element 108 is reduced from an insertion temperature to an operational temperature over a time period that is no greater than one minute. In at least some embodiments, during an ablation procedure the temperature within the expansion element is reduced from an insertion temperature to an operational temperature over a time period that is no greater than two minutes. In at least some embodiments, during an ablation procedure the temperature within the expansion element is reduced from an insertion temperature to an operational temperature over a time period that is no greater than three minutes. In at least some embodiments, during an ablation procedure the temperature within the expansion element is reduced from an insertion temperature to an operational temperature over a time period that is no greater than four minutes. In at least some embodiments, during an ablation procedure the temperature within the expansion element is reduced from an insertion temperature to an operational temperature over a time period that is no greater than five minutes.

Figure 7:
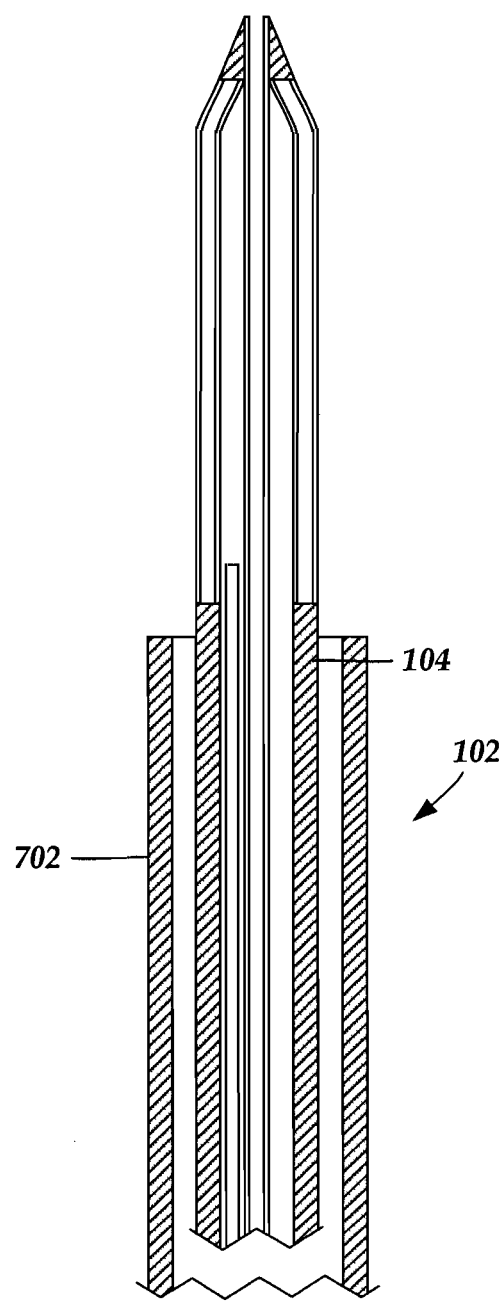
FIG. 7 is a schematic longitudinal cross-sectional view of one embodiment of a distal portion of the catheter of FIG. 2A disposed in a sheath, according to the invention.

In at least some embodiments, a sheath may be used to facilitate guidance of the catheter through patient vasculature during insertion of the catheter. FIG. 7 is a schematic longitudinal cross-sectional view of one embodiment of the distal portion 104 of the catheter 102 disposed in a sheath 702. In at least some embodiments, the sheath 702 is steerable. Once the catheter 102 is positioned at a target location, such as the ostia of the pulmonary veins in the left atrium of the heart of the patient, the sheath 702 can be removed.

The above specification, examples and data provide a description of the manufacture and use of the composition of the invention. Since many embodiments of the invention can be made without departing from the spirit and scope of the invention, the invention also resides in the claims hereinafter appended.

What is claimed is:

1. A cryoablation catheter assembly comprising:
   a catheter having a distal portion, a proximal portion, and a longitudinal length, the catheter configured and arranged for insertion into patient vasculature, the catheter comprising a body and defining at least one coolant outtake region extending along at least a portion of the catheter;
   a rotatable guide tube disposed in the catheter, the guide tube having a proximal end and a distal end, the guide tube extending along at least a portion of the catheter such that the distal end of the guide tube extends beyond the distal portion of the catheter;
   a coolant transfer tube disposed in the catheter, the coolant transfer tube having a distal end, the coolant transfer tube extending along at least a portion of the catheter such that the distal end of the coolant transfer tube extends beyond the distal portion of the catheter, wherein the coolant transfer tube defines a lumen configured and arranged to receive and transfer coolant from a coolant source to the distal end through the coolant transfer tube;
   an expansion element coupled to the distal portion of the catheter, the expansion element having a proximal end, a distal end, and defining an inner expansion-element space, the proximal end coupled to the body of the catheter and the distal end coupled to the guide tube, the inner expansion-element space in fluid communication with the at least one coolant outtake region and the distal end of the coolant transfer tube;
   a rotation system coupleable to, or coupled to, the proximal end of the guide tube, the rotation system configured and arranged to rotate the distal end of the expansion element relative to the proximal end of the expansion element by rotating the guide tube relative to the catheter; and
   wherein the rotation system comprises a linear gear assembly mated with a rotational gear assembly.

2. The cryoablation catheter assembly of claim 1, wherein the rotation system is configured and arranged such that linear movement of the linear gear assembly causes the rotational gear assembly to rotate.

3. The cryoablation catheter assembly of claim 2, wherein the linear gear assembly further comprises a rack gear with a longitudinal length and a tactile control for controlling linear movement of the rack gear along the rotational gear assembly.

4. The cryoablation catheter assembly of claim 3, wherein the rotational gear assembly further comprises a spur gear that mates with the rack gear to convert linear movement of the rack gear to rotational movement of the spur gear.

5. The cryoablation catheter assembly of claim 4, wherein the rotational gear assembly further comprises a shaft having a proximal end and a distal end, wherein the proximal end of the shaft couples to the rotational gear assembly.

6. The cryoablation catheter assembly of claim 5, wherein the rotational gear assembly is configured and arranged such that rotational movement of the spur gear causes rotational movement of the shaft.

7. The cryoablation catheter assembly of claim 6, wherein the distal end of the shaft is coupled to the proximal end of the guide tube.

8. The cryoablation catheter assembly of claim 5, wherein the shaft is parallel to the rack gear.

9. The cryoablation catheter assembly of claim 5, wherein the rotational gear assembly further comprises at least two gears mated together and coupled to the spur gear, the at least two gears mated together to rotate the shaft around an axis parallel to the rack gear.

10. The cryoablation catheter assembly of claim 1, wherein the rotation system is disposed in a handle coupled to the proximal end of the catheter.

11. A cryoablation system comprising:
    a catheter having a distal portion, a proximal portion, and a longitudinal length, the catheter configured and arranged for insertion into patient vasculature, the catheter comprising a body and defining at least one coolant outtake region extending along at least a portion of the catheter;
    a rotatable guide tube disposed in the catheter, the guide tube having a proximal end and a distal end, the guide tube extending along at least a portion of the catheter such that the distal end of the guide tube extends beyond the distal portion of the catheter;
    a coolant transfer tube disposed in the catheter, the coolant transfer tube having a distal end, the coolant transfer tube extending along at least a portion of the catheter such that the distal end of the coolant transfer tube extends beyond the distal portion of the catheter, wherein the coolant transfer tube defines a lumen configured and arranged to receive and transfer coolant from a coolant source to the distal end through the coolant transfer tube;
    an expansion element coupled to the distal portion of the catheter, the expansion element having a proximal end, a distal end, and defining an inner expansion-element space, the proximal end coupled to the body of the catheter and the distal end coupled to the guide tube, the inner expansion-element space in fluid communication with the at least one coolant outtake region and the distal end of the coolant transfer tube; and
    a rotation system coupleable to, or coupled to, the proximal end of the guide tube, the rotation system configured and arranged to rotate the distal end of the expansion element relative to the proximal end of the expansion element by rotating the guide tube relative to the catheter; wherein the rotation system comprises a linear gear assembly mated with a rotational gear assembly;
    a coolant source coupled to the coolant transfer tube;
    a fluid-drawing source coupled to the at least one coolant outtake region;
    and a control module coupled to the catheter, the coolant source, and the fluid-drawing source, wherein the control module comprises a coolant flow controller configured and arranged for controlling the flow of coolant along the coolant transfer tube and the at least one coolant outtake region.

12. The cryoablation system of claim 11, wherein the control module further comprises a pressure sensor for monitoring pressure within the catheter.

13. The cryoablation system of claim 11, wherein the control module further comprises a temperature sensor for monitoring temperature within the catheter.

14. The cryoablation system of claim 11, wherein the coolant source comprises a coolant, the coolant being a liquefied gas under pressure.

15. The cryoablation system of claim 11, wherein the control module is coupled to the rotation system.

* * * * *